United States Patent
Jin et al.

(10) Patent No.: US 11,643,674 B2
(45) Date of Patent: May 9, 2023

(54) METHODS FOR PRE-TREATMENT OF LIGNOCELLULOSE BY ADDING ALKALINE OR ACIDIC REAGENT(S) DURING DENSIFICATION THEREOF AND FOR BIOTRANSFORMATION THEREOF

(71) Applicant: NANJING UNIVERSITY OF SCIENCE AND TECHNOLOGY, Jiangsu (CN)

(72) Inventors: Mingjie Jin, Nanjing (CN); Xiangxue Chen, Nanjing (CN); Xinchuan Yuan, Nanjing (CN)

(73) Assignee: NANJING UNIVERSITY OF SCIENCE AND TECHNOLOGY, Jiangsu (CN)

( * ) Notice: Subject to any disclaimer, the term of this patent is extended or adjusted under 35 U.S.C. 154(b) by 3 days.

(21) Appl. No.: 17/252,168

(22) PCT Filed: Jul. 17, 2019

(86) PCT No.: PCT/CN2019/096329
§ 371 (c)(1),
(2) Date: Dec. 14, 2020

(87) PCT Pub. No.: WO2020/206863
PCT Pub. Date: Oct. 15, 2020

(65) Prior Publication Data
US 2021/0269837 A1    Sep. 2, 2021

(30) Foreign Application Priority Data

Apr. 8, 2019  (CN) .......................... 201910277078.0
Jun. 20, 2019  (CN) .......................... 201910536652.X

(51) Int. Cl.
*C12P 19/14* (2006.01)

(52) U.S. Cl.
CPC ........... *C12P 19/14* (2013.01); *C12P 2201/00* (2013.01); *C12P 2203/00* (2013.01)

(58) Field of Classification Search
CPC .................................. C12P 19/14; C12P 7/10
See application file for complete search history.

(56) References Cited

U.S. PATENT DOCUMENTS

| | | | |
|---|---|---|---|
| 2013/0196398 A1* | 8/2013 | Bals .......................... | C12P 7/10 435/160 |
| 2015/0118349 A1* | 4/2015 | Cecava .................... | C08H 8/00 426/2 |
| 2021/0269837 A1* | 9/2021 | Jin .......................... | C12P 19/14 |

FOREIGN PATENT DOCUMENTS

| | | |
|---|---|---|
| CN | 102010882 A | 4/2011 |
| CN | 104284983 A | 1/2015 |
| CN | 104334030 A | 2/2015 |
| CN | 104805151 A | 7/2015 |
| CN | 106191158 A | 12/2016 |
| CN | 106636226 A | 5/2017 |
| WO | WO 2013/163571 A2 | 10/2013 |

OTHER PUBLICATIONS

International Search Report issued in PCT/CN2019/096329 (PCT/ISA/210), dated Jan. 10, 2020.
Iroba et al., "Producing durable pellets from barley straw subjected to radio frequency-alkaline and steam explosion pretreatments," International Journal of Agricultural and Biological Engineering, vol. 7, No. 3, Jun. 2014, pp. 68-82.
Li et al., "Responses of biomass briquetting and pelleting to water-involved pretreatments and subsequent enzymatic hydrolysis," Bioresource Technology, vol. 151, 2014, pp. 54-62.
Sundaram et al., "Understanding the Impacts of AFEX Pretreatment and Densification on the Fast Pyrolysis of Corn Stover, Prairie Cord Grass, and Switchgrass," Applied Biochemistry and Biotechnology, vol. 181, 2017, pp. 1060-1079.

* cited by examiner

*Primary Examiner* — Tekchand Saidha
(74) *Attorney, Agent, or Firm* — Birch, Stewart, Kolasch & Birch, LLP

(57) ABSTRACT

Disclosed are methods for the pre-treatment of lignocellulose by adding an alkali or acid reagent(s) during the densification thereof, and for the biotransformation thereof. In the method, an alkali reagent(s) or acid reagent(s) is added to a lignocellulosic raw material for a densification pre-treatment to form an alkali- or acid-containing densified lignocellulose with a compressed compact shape, thereby achieving the pre-treatment. The acid or alkali in the pre-treated lignocellulose can further pre-treat the lignocellulosic raw material in a mild manner during the subsequent transportation and storage processes. If a subsequent pre-treatment is needed, then the severity thereof is reduced substantially; in addition, the uniform mixing of the acid or alkali with the lignocellulose and a large density of the raw material promote a high efficiency and a high loading capacity of the subsequent pre-treatment of the densified lignocellulose. The method is simple and efficient. The resulting lignocellulosic raw material has a large density, will not easily degrade or rot due to the inclusion of an acid or alkali, which is conducive to transportation and storage, and a high equipment utilization rate during the subsequent treatment is achieved.

20 Claims, 6 Drawing Sheets

METHODS FOR PRE-TREATMENT OF LIGNOCELLULOSE BY ADDING ALKALINE OR ACIDIC REAGENT(S) DURING DENSIFICATION THEREOF AND FOR BIOTRANSFORMATION THEREOF

TECHNICAL FIELD

The invention, involving a method for pretreating a lignocellulose with an alkaline reagent(s) or an acidic reagent(s) during densification and for biotransformation thereof, belongs to the technical field of biorefining.

BACKGROUND OF THE INVENTION

Lignocellulose is one of the most abundant renewable resources in nature, which is widely distributed and easy to obtain. Biorefinery of lignocellulose for various bioproducts production can not only help to guarantee energy security, promote rural economy development, but also reduce greenhouse gas emission, protect the environment and promote sustainable development.

Lignocellulose has a property of low density and prone to mold, deterioration, and decay, which leads to high costs of transportation and storage, and which to some extent impedes the industrialization of lignocellulose biorefinery. Pretreatment of the lignocellulose is a necessary step for biorefining to produce target products such as biofuels, which is to disrupt plant cell wall structure and reduces the recalcitrance of lignocellulose for bioconversion. Traditional pretreatment methods have disadvantages such as serious corrosion to pretreatment reaction equipment, low safety, high energy consumption and cumbersome operation, etc. (referring to Theerarattananoon K, Xu F, Wilson J, et al. Effects of the pelleting conditions on chemical composition and sugar yield of corn stover, big bluestem, wheat stover, and sorghum stover pellets[J]. Bioprocess BiosystEng, 2012, 35(4):615-623). In addition, the low density and loose property of the lignocellulose also limit loading capacity in the equipment during pretreatment and bio-transformation, resulting in low productivity, low equipment utilization, and high cost of pretreatment.

The lignocellulose can be densified to have a dense structure which can increase lignocellulose density to 5-15 folds and thus substantially reduces the cost of storage by 50% and the cost of transportation by 90%. Furthermore, the densified lignocellulose owns the same shapes and sizes, which facilitates operations for industrial production (referring to Zhang P F, Zhang Q, Deines T W, et al. Ultrasonic Vibration-Assisted Pelleting of Wheat Stover: A Designed Experimental Investigation on Pellet Quality and Sugar Yield, Asme International Manufacturing Science& Engineering Conference. 2012 Theerarattananoon K, Xu F, Wilson J, et al. Effects of the pelleting conditions on chemical composition and sugar yield of corn stover, big bluestem, wheat stover, and sorghum stover pellets[J]. Bioprocess BiosystEng, 2012, 35(4):615-623.) Densified lignocellulose significantly increases the lignocellulose loading in a reactor during pretreatment and thus significantly increases the utilization rate of equipment volume (referring to Venkatesh Balan, Sugarland, Tex. (US); Leonardo da Costa Sousa, Brighton, Mich. (US), De-esterification of biomass prior to ammonia pretreatment and systems and products related thereto[P], application Ser. No. 16/029,452, 2018 Jul. 6), which at the same time facilitates operations in the subsequent biotransformation process and is beneficial to increase the concentration of the substrate (Bals B D, Gunawan C, Moore J, et al. Enzymatic Hydrolysis of Pelletized AFEX TM-Treated Corn Stover at High Solid Loadings[J]. Biotechnology & Bioengineering, 2013, 111(2):264-271). Densification can also be carried out after the pretreatment of the lignocellulosic raw materials. In research by Bruce E. Dale, it was found that corn stover densified after AFEX (Ammonia Fiber Explosion) pretreatment, which is conducive to enzymatic hydrolysis with high substrate concentrations and convenient for feeding (Brian Bals, Fazzanet Tamori, Timothy J. Campbell, Bruce E. Dyer, Methods of hydrolyzing pretreated densified biomass particulates and systems related thereto [P], Chinese Patent: CN 201380022053.7, 2013 Apr. 26).

Although densified lignocellulose is beneficial to increase the loading of raw materials during pretreatment, it requires an increase in pretreatment conditions, such as an increase in temperature and an extension of reaction time (Venkatesh Balan, Sugarland, Tex. (US); Leonardo da Costa Sousa, Brighton, Mich. (US), De-esterification of biomass prior to ammonia pretreatment and systems and products related thereto[P], application Ser. No. 16/029,452, 2018 Jul. 6). At the same time, there are mass transfer problems for the chemical reagents and the densified lignocellulose during the pretreatment: due to the dense structure, it is difficult for the chemical reagents to penetrate into the densified stover, which often leads to unsatisfactory pretreatment effects or requires more demanding pretreatment conditions. In addition, heat transfer problem may also cause a temperature difference between the inside and outside of the densified lignocellulosic raw material, thereby affecting the pretreatment effect.

SUMMARY

In view of the existing problems of high cost for transportation and storage of lignocellulose, high requirements for pretreatment equipment, high energy consumption, mass transfer and heat transfer issues for pretreating densified lignocellulose, the present application provides a method for pretreating lignocellulose with an alkaline reagent(s) or an acidic reagent(s) during densification thereof and for biotransformation thereof. The lignocellulose can be pretreated by adding the alkaline reagent(s) or the acidic reagent(s) during the lignocellulose densification process. The alkaline reagent(s) or acidic reagent(s) in the densified lignocellulose further has relatively mild pretreatment effects on the lignocellulose raw materials in the subsequent transportation and storage, so as to further improve the pretreatment effect during the transportation and storage time. An acid- or base-containing densified lignocellulose is not easy for mold deterioration, and decay, and the increase of density of the lignocellulose is more suitable for storage and transportation. In the present application, it avoids the requirements of traditional technology on pretreatment equipment and energy consumption. In addition, if further pretreatment is required, the severity of reaction conditions for further pretreatment can be reduced to a certain extent, and the mass transfer problem of chemical reagents during the pretreatment process of densified lignocellulose can be solved at the same time. When the lignocellulose densified with the alkaline agent is further pretreated, the addition of water incurs heat generation (the alkali is exothermic in contact with water), which solves the problem of heat transfer during the pretreatment of the densified lignocellulose to a certain extent. Therefore, the effect of further pretreatment will also be greatly improved.

The present application has the technical solution as follows:

A method for pretreating lignocellulose with an alkaline reagent(s) or an acidic reagent(s) during densification, comprises adding the alkaline reagent(s) or acidic reagent(s) during the densification of a lignocellulose raw material; or adding the alkaline reagent(s) or acidic reagent(s) into the lignocellulose raw material, mixing evenly, and then conducting densification treatment; or adding the alkaline reagent(s) or acidic reagent(s) into the lignocellulose raw material for reaction and then performing a densification treatment to obtain an acid- or base-containing densified lignocellulose.

Furthermore, a method for bio-transforming an acid- or base-containing densified lignocellulose, comprising adding the alkaline reagent(s) or acidic reagent(s) during the densification of a lignocellulose raw material; or adding the alkaline reagent(s) or acidic reagent(s) into the lignocellulose raw material, mixing evenly, and then conducting densification treatment; or adding the alkaline reagent(s) or acidic reagent(s) into the lignocellulose raw material for reaction and then performing a densification treatment to obtain an acid- or base-containing densified lignocellulose, which can be directly bio-transformed or further selectively pretreated for a subsequent biotransformation.

In the present application, the lignocellulose is selected from one or more of the following: wheat straw, corn stover, agricultural and forestry waste, rice straw, sorghum stover, soybean stover, forestry waste, recycled wood pulp fiber, wood chips, softwood, hardwood, aquatic weed, aquatic plants, algae, animal feces and combinations thereof, and the lignocellulose has a water/moisture content of 0%-90%.

In the present application, the alkaline reagent(s) is selected from one or more of the following: sodium hydroxide, calcium hydroxide, potassium hydroxide, sodium sulfite, sodium bisulfite, sodium acetate, sodium carbonate, sodium bicarbonate, sodium sulfate, ethylenediamine, triethylamine, ammonia water, liquid ammonia, calcium oxide, and sodium oxide, and combinations thereof.

In the present application, the acidic reagent(s) is selected from one or more of the following: sulfuric acid, nitric acid, nitrous acid, hydrochloric acid, phosphoric acid, sulphurous acid, perchloric acid, chloric acid, chlorous acid, hypochlorous acid, oxalic acid, formic acid, acetic acid, propionic acid, benzoic acid, phenylacetic acid, benzenesulfonic acid, oxalic acid, succinic acid, carbon dioxide, sulfur dioxide, sodium bisulfate, sodium bisulfite, and combinations thereof.

In the present application, the dosage of alkaline reagent(s) or acidic reagent(s) is 0.5%-30.0% of the lignocellulose dry weight.

In the present application, the alkaline reagent(s) or acidic reagent(s) can be directly added in the form of a pure base reagent(s) or acidic reagent(s), or in the form of an aqueous solution of the alkaline or acidic reagent(s); the alkaline reagent(s) or acidic reagent(s) can be directly poured or added, sprayed, brought in via steam, or sprayed as an alkaline or acidic gas, such that the alkaline or acidic reagent(s) can be fully mixed with the lignocellulose for performing lignocellulose densification treatment; or during the densification, the alkaline reagent(s) or acidic reagent(s) and the lignocellulose are added to a densification equipment to produce a densified lignocellulose with a dense shape.

In the present application, the acid- or base-containing densified lignocellulose without further pretreatment can be subjected to biotransformation immediately or after standing for a certain period of time. The acid- or base-containing densified lignocellulose can be further selectively pretreated for the subsequent biotransformation, and the further selective pretreatment of densified lignocellulose is selected from the following: spraying water on the lignocellulose, steaming, soaking, sun exposure, freezing, high temperature treatment, cooking in water, high temperature sterilization, microwave, or ultrasonic treatment; or hydrothermal pretreatment including steam explosion, hot water pretreatment, and steam pretreatment; acidic pretreatment, including dilute acid pretreatment, weak acid pretreatment, oxidative acid pretreatment, mixed acid pretreatment; or alkaline pretreatment, including dilute alkaline pretreatment, weak alkaline pretreatment, ammonia pretreatment, oxidative alkaline pretreatment, or mixed alkaline pretreatment, and organic solvent pretreatment.

In the present application, the densified lignocellulose has a density of 200-1500 kg/m$^3$, and the densified lignocellulose has a rod shape with a diameter of 1 mm-30 cm; a granule shape with a diameter of 0.1 cm-50 cm; a block shape with a length of 0.1 cm-200 cm, a width of 0.1 cm-200 cm, and a height of 0.1 cm-200 cm; or a pellet shape with a diameter of 0.1 cm-50 cm and a thickness of 0.01 cm-20 cm.

In the present application, the biological transformation comprises an enzymatic reaction comprising adding enzymes or fermentation in a pretreatment substrate, wherein the enzyme is selected from one or more of cellulase, hemicellulase, pectinase, xylanase, amylase and saccharification enzyme, and/or a microbial transformation which is a microorganism fermentation comprising adding a fermenting microorganism into a pretreatment substrate or enzymatic hydrolysate, and the fermenting microorganism is selected from one or more of yeast, bacteria, and mold.

In the present application, the biotransformation has a product comprising biofuels, commodity chemicals, fine chemicals, animal feeds, food additives or medicines, etc., such as ethanol, butanol, acetone, acetic acid, lactic acid, aliphatic hydrocarbon, lipids, proteins, amino acids, enzymes, antibiotics, vitamins, antibodies, and methane.

In the present invention, the alkaline reagent(s) or acidic reagent(s) are added during the densification process of the lignocellulose, which not only utilizes the mechanical action in the densification process and the heat generated in the compression process (together with the acid or alkali) to destroy the structure of the lignocellulose, but also both the alkaline reagent(s) and the acidic reagent(s) can exert chemical effects on the lignocellulose, such that the lignocellulose can be pretreated during the transportation and storage at different temperatures (−40° C.~100° C.), and the pretreated lignocellulose can be directly used in the subsequent biotransformation, or further pretreatment before the biotransformation (at this time, the alkaline reagent(s) or the acidic reagent(s) have been fully mixed with the lignocellulose, which is conducive to further pretreatment with high lignocellulose loading).

The present application has the following advantages relative to the prior art:
(1) The alkaline reagent(s)- or acidic reagent(s)-containing densified lignocellulose prepared in the present application is much more suitable for storage and transportation;
(2) The pretreatment process and the densification process can be performed in one step, which reduces pretreatment cost;
(3) The pretreatment conditions are mild and the time for lignocellulose transportation and storage are fully utilized for pretreatment reactions.

(4) Further treatment, if needed, requires lower reaction intensity (severity of the reaction conditions) with good mass transfer and heat transfer effects;

(5) As the pretreatment intensity is decreased, the inhibitors (degradation products) generated during the pretreatment process might be fewer, which facilitates bio-transformation.

DETAILED DESCRIPTION

In order to facilitate the understanding of the present application, the present application will be described in detail below with reference to the drawings and preferable embodiments of the specification, but the scope of the present application is not limited to the following specific embodiments.

All terms used below have the same meanings as commonly understood by a person skilled in the art, unless otherwise defined. The terminology used herein is only for the purpose of describing specific embodiment, and is not intended to limit the scope of the present application.

Unless otherwise specified, the reagents, raw materials, instruments and equipment used in the present application are commercially available or prepared by existing methods.

The meanings of the abbreviations are listed as follows: PCS: Pelletized Corn stover; DA: Dilute sulfuric Acid pretreatment; AL: Alkaline pretreatment; LHW: Liquid Hot Water pretreatment; DLL: Densifying Lignocellulose with Lime pretreatment: Due to the addition of water during the densification process, the lime becomes calcium hydroxide; DLS: Densifying Lignocellulose with sodium hydroxide pretreatment; DLA: Densifying Lignocellulose with sulfuric acid pretreatment; PCS+AL: Pelletized Corn Stover pretreated by Dilute ALkali; DLA+LHW: Densifying Lignocellulose with sulfuric Acid followed by Liquid Hot Water; DLS+Autoclave: Densifying Lignocellulose with Sodium hydroxide followed by autoclave; DLL+LHW: Densifying Lignocellulose with Lime followed by Liquid Hot Water pretreatment.

In the following examples, a granulator is used for densification during the densification process.

Example 1

Example 1 is to show that the effect of adding alkali or acid during the densification of corn stover on the storage or transportation of the raw materials, which comprises the following steps:

1. Raw materials preparation: the corn stover in the field was harvested, dried naturally, and then milled to particles with diameters of 1-4 mm.

2. Densification pretreatment: the milled corn stovers were divided into three groups which were sprayed with sodium hydroxide solution, sulfuric acid solution and pure water, respectively. The dosage for sodium hydroxide was 0.3 g/g dry biomass, and the dosage for sulfuric acid was 0.1 g/g dry biomass. The water content was all 0.5 g/g dry biomass for the above three ways of densification. The corn stover uniformly mixed with reagents was then pelletized in a pellet granulator, and then stored at room temperature for 6 days.

Figure 1:
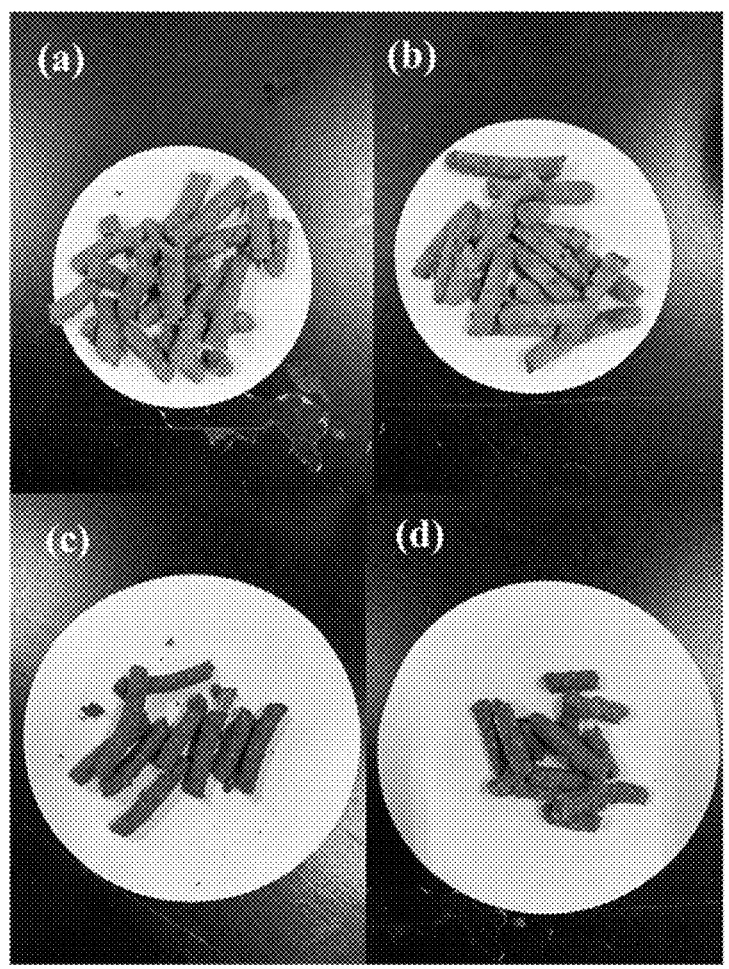
FIG. 1, (a) shows the surface morphology of the corn stover particles densified without alkaline agent in Example 1 on day 1; (b) shows the surface morphology of the corn stover particles densified without alkaline agent on day 6 at room temperature; (c) shows the surface morphology of the pretreated corn stover particles with sodium hydroxide (0.3 g/gram of the dry weight of corn stover) added during densification on day 1, (d) shows the surface morphology of the corn stover particles densified with the sodium hydroxide (0.3 g/gram of dry weight of corn stovers) at room temperature for 6 days.
Figure 2:
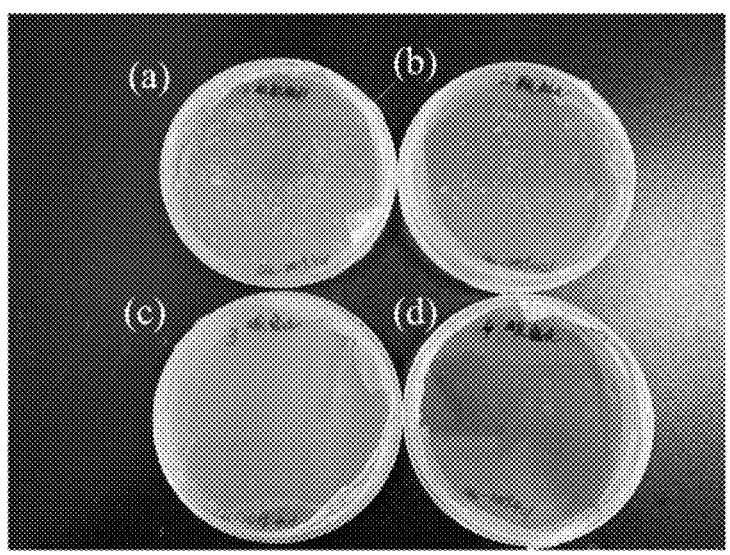
FIG. 2, (a) shows the growth state of microbes from a supernatant sample of the loose corn stover without chemical reagents in Example 1 on a LB solid medium plate; (b) shows microbes from a supernatant sample of the densifying treated corn stover without chemical reagents added during densification on a LB solid medium plate; (c) shows the growth state of the microbes from a supernatant sample of the densifying pretreated corn stover with the alkaline reagent added during densification on a LB solid medium plate; (d) shows the growth state of the microbes from a supernatant sample of the pretreated corn stover with the acidic reagent added during densification on a LB solid medium plate.

3. Plating process: the corn stover densified with sodium hydroxide (DLS), the corn stover densified with sulfuric acid (DLA), and the corn stover densified without chemical reagents were uniformly mixed with sterile water, respectively. The ratio of stover dry mass to water is 1:20; and 10 µL of supernatant of each group is taken and diluted to plate on the LB solid medium for cultivation in a constant temperature incubator at 30° C. for 3 days;

In Example 1, the growth status of microbes from the corn stovers densified with or without chemical reagents at different storage times is shown in FIG. 1. FIG. 1($a$) shows the surface phenomenon of the corn stover particles densified without alkaline reagent in Example 1 on day 1; (b) shows the surface phenomenon of the corn stover particles densified without alkaline reagent on day 6 at room temperature; (c) shows the surface phenomenon of the pretreated corn stover particles with sodium hydroxide (0.3 g/gram of the dry weight of corn stover) added during densification on day 1, (d) shows the surface phenomenon of the corn stover particles densified with the sodium hydroxide (0.3 g/g dry weight of corn stovers) at room temperature on day 6. As shown in (a) and (b) in FIG. 1, for the corn stover that was densified without the addition of alkaline reagents, there were microbes growing on the surface of the corn stover on day 6, while (c) and (d) in Figures show no microbes on the surface of the corn stover densified with alkaline reagents. FIG. 2 shows the growth states of the microbes from the supernatant of the corn stover densified with or without chemical reagents with the addition of a certain proportion of sterile water. As shown in FIG. 2, (a) shows the growth state of microbes from a supernatant sample of the loose corn stover without chemical reagents in Example 1 on a LB solid medium plate; (b) shows microbes from a supernatant sample of the pretreated corn stover without chemical reagents added during densification on a LB solid medium plate; (c) shows the growth state of the microbes from a supernatant sample of the pretreated corn stover with the alkaline reagent added during densification on a LB solid medium plate; (d) shows the growth state of the microbes from a supernatant sample of the pretreated corn stover with the acidic reagent added during densification on a LB solid medium plate. As shown in FIG. 2, there was no colony grown on the plate of the corn stover pretreated with alkali or acid during densification, but the plates of the loose corn stover and the corn stover pretreated without chemical reagents during the densification grew out many microbial colonies to different extents, which means that the corn stovers that are pretreated by adding acidic or alkaline reagents during densification can inhibit the growth of microbes during storage and transportation, thereby preventing rot or mold growing of the raw materials, and reducing the adverse effects on industrial production.

Example 2

Example 2 is intended to show that effects of adding alkali or acid during the densification of corn stover on reducing the costs of the storage or transportation of the raw materials, which comprises the following steps:

1. Raw materials preparation:
the corn stover was harvested in the field, dried naturally and then milled to particles with diameters of 1-4 mm.

2. Densification pretreatment: the milled corn stovers were divided into two groups which were sprayed with sodium hydroxide solution or sulfuric acid respectively. The dosage for sodium hydroxide was 0.3 g/g dry biomass. The dosage for sulfuric acid was 0.1 g/g dry biomass. The water content was 0.5 g/g dry biomass for the above two ways of densification. The corn stover uniformly mixed with reagents was then pelletized in a pellet granulator to perform a densification process.

Figure 3:
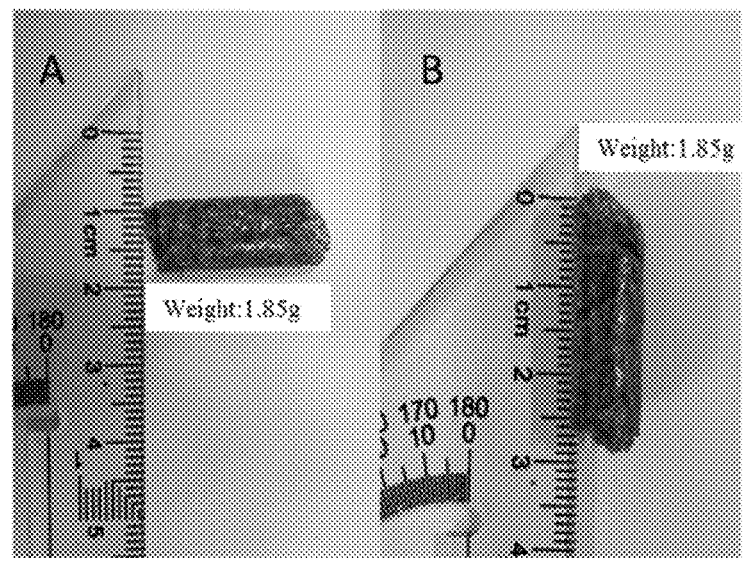
FIG. 3, (A) shows the diameter of the pretreated corn stover in Example 2 with alkaline reagent or the acidic reagent added during densification. (B) shows the length of the pretreated corn stover with alkaline reagent or the acidic reagent added during densification.

In Example 2, adding alkali or acid during the densification of corn stover reduces the costs of storage or transportation. In FIG. 3, (A) shows the diameter of the pretreated corn stover with alkaline reagent or the acidic reagent during densification. (B) shows the length of the pretreated corn stover with alkaline reagent or acidic reagent added during densification; in FIG. 4, (A) shows the loose corn stover in a 100 ml plastic cup; B shows the pretreated corn stover with acid added during densification in a 100 ml plastic cup. As shown in FIG. 3, the corn stover densifying pretreated with acidic reagent has a diameter of around 0.8 cm, a length of about 2.5 cm and a mass of 1.85 g. then the volume thereof is $$\pi * 2.5 * \left(\frac{0.8}{2}\right)^2 = 1.256 \text{ mL},$$

and density thereof is $$\frac{1.85 * 1000}{1.256} = 1473 \text{ kg/m}^3$$

Figure 4:
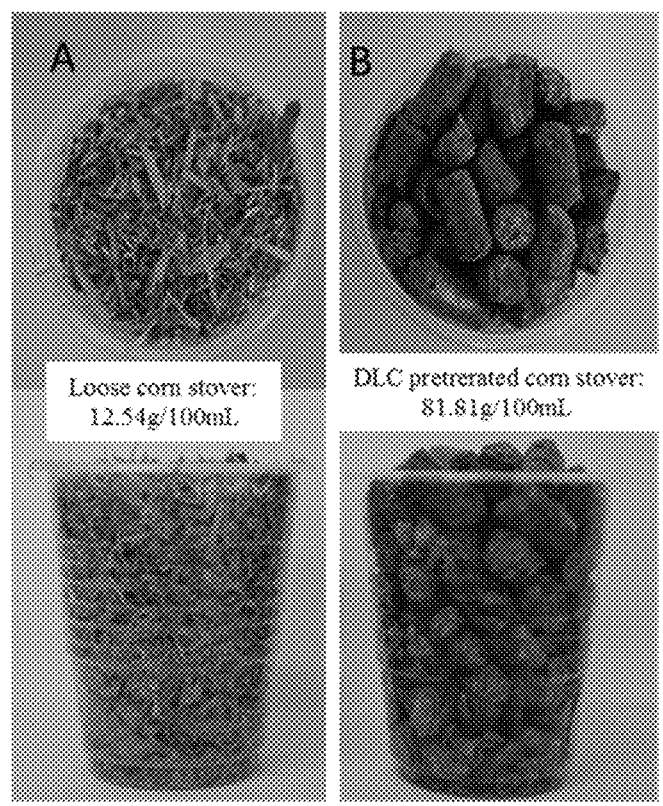
FIG. 4, (A) shows the loose corn stover in a 100 ml plastic cup; (B) shows the pretreated corn stover with acid added during densification in a 100 ml plastic cup.

As shown in FIG. 4, the 100 ml plastic cup fully filled with loose corn stover weighs 12.54 g, while the same cup fully filled with the corn stover densifying pretreated with the acid weighs 81.81 g. Therefore, the corn stover densifying pretreated with acid has a density around 6.5 times the density of the loose corn stover, which indicates corn stover densifying pretreated with acid or base has great advantage in transportation and storage relative to the loose corn stover.

Example 3

Example 3 shows the effects of storage time of the densifying Lignocellulose with Lime (DLL) pretreated corn stover on its enzymatic hydrolysis, which comprises the following steps:

1. Raw materials preparation: the corn stover in the field was harvested, dried naturally, and then milled to particles with diameters of 1-4 mm.

2. DLL pretreatment: the milled corn stover was placed in a sealed bag and sprayed uniformly with calcium hydroxide solution. The amount of calcium hydroxide and water dosed depend on the dry weight of the corn stover. The dosage of the calcium hydroxide was 0.15 g/g dry corn stover biomass, and the water content was 0.5 g/g dry biomass. The densification process is performed at room temperature, and the densified corn stover was stored at room temperature for 0, 6 and 12 days.

3. The densified corn stovers stored for different days were enzymatically hydrolyzed at 3% (wt/wt, the corn stover is 3% weight percentage of the total weight of the stover, water, hydrolase and the chemical reagents) substrate concentration in an enzymatic hydrolysis reactor. Enzymatic hydrolysis was performed at 50° C. and 250 rpm in a shake incubator for 24 hours using hydrolase and citrate buffer.

Example 3 shows the effects of storage time of the densifying Lignocellulose with Lime (DLL) pretreated corn stover on its enzymatic hydrolysis.

Figure 5:
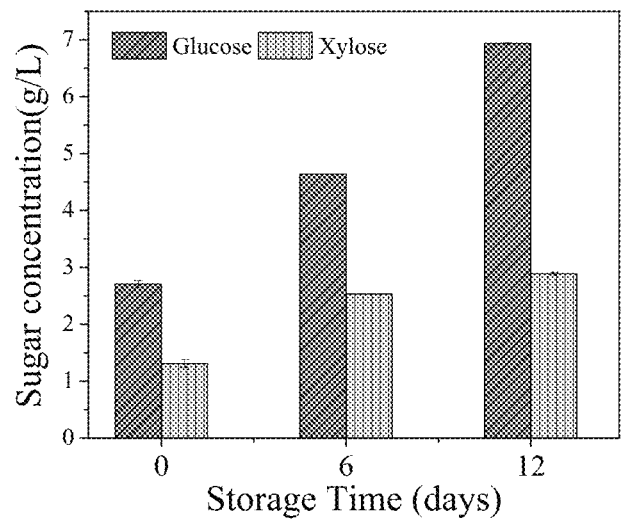
FIG. 5 shows the effect of different storage time (0, 6, 12 days) of the pretreated corn stover with calcium hydroxide added during densification (DLL) on enzymatic hydrolysis in Example 3.
Figure 6:
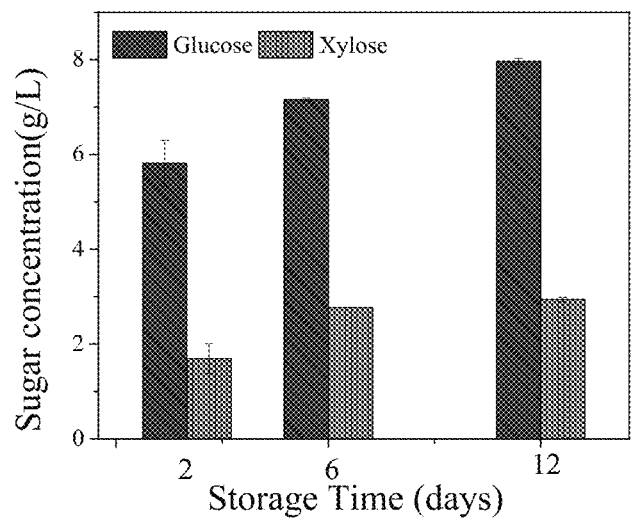
FIG. 6 shows the effect of different storage time (2, 6, 12 days) of the pretreated corn stover with sodium hydroxide added during densification (DLS) on enzymatic hydrolysis in Example 4.

As shown in FIG. 5, "▨" represents the concentration of glucose enzymatically hydrolyzed from the corn stover pretreated with calcium hydroxide during densification; "▨" represents the concentration of xylose enzymatically hydrolyzed from the corn stover pretreated with calcium hydroxide during densification. As shown in FIG. 5, with the increase of storage days of the corn stover, the concentrations of the glucose and xylose released from enzymatic hydrolysis increased. For the corn stover stored for 12 days, the corn stover with 3% substrate concentration can be enzymatically hydrolyzed to have a glucose concentration of 6.9 g/L and a xylose concentration of 2.8 g/L, which indicates that the calcium hydroxide destroys original compact structure of the corn stover during storage.

Example 4

Example 4 shows the effects of storage time of the densifying Lignocellulose with sodium hydroxide (DLS) pretreated corn stover on its enzymatic hydrolysis, which comprises the following steps:

1. Raw materials preparation: the corn stover in the field was harvested, dried naturally, and then milled to particles with diameters of 1-4 mm.

2. DLS pretreatment: the milled corn stover was placed in a sealed bag and sprayed uniformly with sodium hydroxide solution. The amount of sodium hydroxide and water used depends on the dry weight of the corn stover. The dosage of the sodium hydroxide was 0.3 g/g dry corn stover biomass, and the water content was 0.5 g/g dry corn stover biomass. The densification process is performed at room temperature, and the densified corn stover was stored at room temperature for 0, 6 and 12 days.

3. The densified corn stovers stored for different days were enzymatically hydrolyzed at 3% (wt/wt, the corn stover is 3% weight percentage of the total weight of the stover, water, hydrolase and the chemical reagents) substrate concentration in an enzymatic hydrolysis reactor. Enzymatic hydrolysis was performed at 50° C. and 250 rpm in a shake incubator for 24 hours with addition of hydrolase and citrate buffer.

Example 4 shows the effects of storage time of the densifying Lignocellulose with Lime (DLL) pretreated corn stover on its enzymatic hydrolysis. As shown in FIG. 4, "▨" represents the concentration of glucose enzymatically hydrolyzed from the corn stover densifying pretreated with sodium hydroxide; "▨" represents the concentration of xylose enzymatically hydrolyzed from the corn stover densifying pretreated with sodium hydroxide. As shown in FIG. 5, with the increase of storage days of the corn stover, the concentrations of the glucose and xylose released during enzymatic hydrolysis increased. For the corn stover stored for 12 days, the corn stover with 3% substrate concentration can be enzymatically hydrolyzed to have a glucose concentration of 8.0 g/L and a xylose concentration of 3.0 g/L, which indicates that the sodium hydroxide destroys original compact structure of the corn stover during storage, achieving the goal of improving enzymatic hydrolysis.

Example 5

Example 5 is to compare the enzymatic hydrolysis effects of Densifying Lignocellulose with sulfuric Acid followed by Liquid Hot Water (DLA+LHW) pretreated corn stover and the traditional dilute acid (DA) pretreated corn stover under the same pretreatment conditions.

1. Raw materials preparation: the corn stover was harvested in the field, dried naturally and then milled to particles with diameters of 1-4 mm.

2. DLA pretreatment: the milled corn stover was sprayed with sulfuric acid. The dosage of sulfuric acid was 0.1 g/g dry biomass, and water content was 0.5 g/g dry biomass. The corn stover uniformly mixed with the acid reagent was then pelletized in a pellet granulator to perform a densification operation. The densified corn stover with sulfuric acid was stored and sealed in a bag at room temperature for at least one day.

3. DLA+LHW pretreatment: corn stover densifying pretreated with acid with a acid concentration of 0.1 g acid/g dry biomass is arranged in a high-temperature and high-pressure reactor for heating, the heating temperature is 160° C., and the reaction time is 10 minutes, wherein the dry weight of the stover: the total water is 1:9.

4. DA (traditional acid pretreatment method) pretreatment: the loose stover is used as raw materials, to which sulfuric acid solution is added, arranged in a high-temperature and high-pressure reactor for heating, the heating temperature is 160° C., and the reaction time is 10 minutes, and the dry weight of the stover: the total water content is 1:9.

5. Enzymatic hydrolysis process: the pretreated corn stover was enzymatically hydrolyzed at 10% (wt/wt, the corn stover is 10% weight percentage of the total weight of the stover, water, hydrolase and the chemical reagents) substrate concentration with addition of hydrolase and Citrate buffer, arranged in a shake incubator at 50° C. and 250 rpm for 72 hours.

Figure 7:
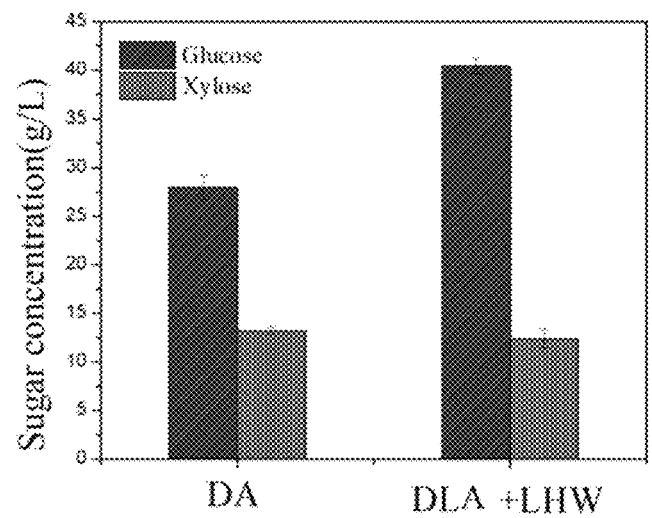
FIG. 7 shows sugar concentrations after enzymatic hydrolysis of the corn stover for 72 hours at 10% substrate concentration (wt/wt, the corn stover is 10% weight percent of the total weight of the stover, water, hydrolase and the chemical reagents), before which the corn stover is pretreated with dilute acid (DA) or densified with acid followed by hot water treatment (DLA+LHW).

In Example 5, it compares, under the same pretreatment conditions, the enzymatic hydrolysis results of DLA+LHW pretreated and DA pretreated corn stover. As shown in FIG. 7, "▨" represents the concentration of glucose during enzymatic hydrolysis; "▨" represents the concentration of xylose during enzymatic hydrolysis of corn stover. As shown in FIG. 7, enzymatic hydrolysis of DLA+LHW pretreated corn stover can be enzymatically hydrolyzed to release 40 g/L glucose, which was substantially higher than that obtained by enzymatic hydrolysis of DA pretreated corn stover (28 g/L), and 12 g/L xylose, which was similar to that achieved by DA pretreated corn stover. In summary, DLA+LHW destroys the structure of the corn stover more thoroughly than traditional dilute acid pretreatment (DA), and releases more hydrolyzable polysaccharides, which is conducive to subsequent operations and shows that the Densifying Lignocellulose with sulfuric Acid pretreatment (DLA) has great potential for industrial application.

Example 6

In Example 6, it compares the enzymatic hydrolysis results of alkaline (AL) pretreated corn stover, pelletized and then alkaline pretreated corn stover (PCS+AL), and Densifying Lignocellulose with sodium hydroxide (DLS) pretreated followed by autoclaved (DLS+Autoclave) corn stover at 6% glucan concentration (wt/wt, glucan is 6% weight percentage of the total weight of the stover, water, hydrolase and the chemical reagents).

1. Raw materials preparation: the corn stover was harvested in the field, dried naturally, and then milled to particles with diameters of 1-4 mm.

2. DLS pretreatment: the milled corn stover was sprayed with sodium hydroxide solution, the dosage of the sodium hydroxide was 0.1 g/g dry corn stover biomass, and the water content was 0.5 g/g dry corn stover biomass. The corn stover uniformly mixed with sodium hydroxide is densified in a pellet granulator, and after the densification, the corn stover was stored and sealed in a bag for more than 1 day.

3. DLS+Autoclave pretreatment: the corn stover densifying pretreated with sodium hydroxide with a sodium hydroxide dosage of 0.1 g/g dry corn stover biomass was autoclaved at 120° C. for 60 min in an autoclave with 30% of (wt/wt, the percentage of the dry weight of corn stover to the total weight) dry weight of the corn stover.

4. PCS+AL pretreatment: the corn stover densifying pretreated without sodium hydroxide was mixed uniformly with a sodium hydroxide solution to reach a solid loading of 20% (wt/wt, the percentage of the dry weight of corn stover to the total weight). The mixture was then autoclaved at 120° C. for 120 min. The sodium hydroxide dosage was 0.1 g/g dry biomass.

5. AL pretreatment: the loose corn stover was mixed with a sodium hydroxide solution to reach a solid loading of 10% (wt/wt, the percentage of the dry weight of corn stover to the total weight). The mixture was then autoclaved at 120° C. for 20 min. The sodium hydroxide dosage was 0.2 g/g dry biomass.

6. Enzymatic hydrolysis process: enzymatic hydrolysis of pretreated corn stover was performed at 6% (wt/wt, the percentage of the glucan to the total weight of the stover, water, hydrolase and the chemical reagents) glucan substrate concentration using hydrolase and citric acid-sodium citrate buffer in a shake incubator at 50° C. and 250 rpm for 24 h.

In Example 6, it compares the enzymatic hydrolysis results of alkaline (AL) pretreated corn stover, pelletized and then alkaline pretreated corn stover (PCS+AL), and DLS pretreated followed by autoclaved (DLS+Autoclave) corn stover at 6% glucan concentration (wt/wt, glucan is 6% weight percentage of the total weight of the stover, water, hydrolase and the chemical reagents).

Figure 8:
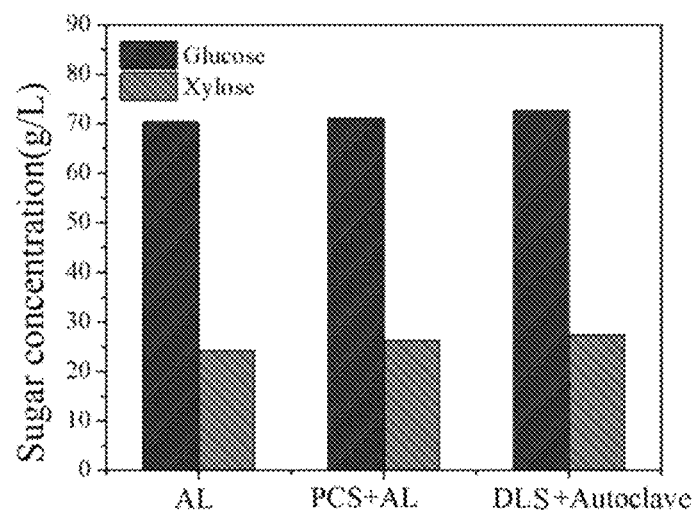
FIG. 8 shows the sugar concentrations of the corn stover after enzymatic hydrolysis at 6% glucan concentration (wt/wt, glucan is 6% weight percentage of the total weight of the stover, water, hydrolase and the chemical reagents) for 24 hours in Example 6, before which the stover is pretreated with dilute alkali (AL), densified and then pretreated with dilute alkali (PCS+AL) and densified with a base followed by sterilization (DLS+Auctoclave).

The sugar concentrations obtained from enzymatic hydrolysis are shown in FIG. 8. "▨" indicates the concentration of glucose in the enzymatic hydrolysate; "▨" indicates the concentration of xylose in the enzymatic hydrolysate.

AL, PCS+AL and DLS+Autoclave pretreatments resulted in similarly high sugar concentrations. However, the sodium hydroxide dosage for DLS+Autoclave and PCS+AL was 50% of that used for AL, and the substrate concentration during pretreatment for DLS+Autoclave and PCS+AL was 100% and 200% higher, respectively, than that used for AL. DLS+Autoclave had a higher substrate concentration during pretreatment than that of the PCS+AL, and used half of the autoclave time compared to PCS+AL. AL and PCS+AL are traditional dilute alkaline pretreatment methods, and DLS+Autoclave as the pretreatment method of the present application not only increases the concentration of the pretreatment substrate, but also reduces the usage amount of chemical reagents and pretreatment intensity, which has important meaning for fuel ethanol promotion.

Example 7

In Example 7, it compares the enzymatic hydrolysis results of DLA pretreated followed by liquid hot water treated (DLA+LHW) corn stover, pelletized and then dilute acid pretreated corn stover (PCS+DA), and dilute acid (DA) pretreated corn stover at 20% (wt/wt, the corn stover is 20% weight percentage of the total weight of the stover, water, hydrolase and the chemical reagents) substrate concentration.

1. Raw materials preparation: the corn stover was harvested in the field, dried naturally, and then milled to particles with diameters of 1-4 mm.

2. DLA pretreatment: the milled corn stover was sprayed with sulfuric acid. The dosage for sulfuric acid was 0.1 g/g dry biomass. The final water content was 0.5 g/g dry biomass. The corn stover uniformly mixed with the acid reagent was then pelletized in a pellet granulator to perform a densification operation. After densification, the corn stover was stored in a sealed bag at room temperature for at least a day before use.

3. DLA+LHW pretreatment: corn stover densifying pretreated with acid with an acid concentration of 0.1 g acid/g dry biomass is arranged in a high-temperature and high-pressure reactor for heating, the heating temperature is 160° C., and the reaction time is 10 minutes, wherein the dry weight of the stover: the total water is 1:5.

4. PCS+DA pretreatment: the corn stover densifying pretreated without acid as the raw material was mixed with a sulfuric acid solution. The mixture was then heated to 160° C. and maintained at 160° C. for 10 min. The sulfuric acid dosage was 0.1 g/g dry corn stover. The final water in the reaction system was 5 times of the dry weight of PCS.

5. DA pretreatment: the loose corn stover as the raw material was mixed with a sulfuric acid solution. The mixture was then heated to 160° C. and maintained at 160° C. for 10 min. The sulfuric acid dosage was 0.1 g/g dry corn stover. The final water in the reaction system was 9 times of the dry weight of CS.

6. Enzymatic hydrolysis process: enzymatic hydrolysis of pretreated corn stover was performed at 20% substrate concentration (wt/wt, the corn stover is 20% weight percentage of the total weight of the stover, water, hydrolase and the chemical reagents) using hydrolase and pure water at 50° C. and 250 rpm in a shake incubator for 72 h.

In Example 7, it compares the enzymatic hydrolysis results of DLA pretreated followed by liquid hot water treated corn stover (DLA+LHW), pelletized and then dilute acid pretreated (PCS+DA) corn stover, and dilute acid (DA) pretreated corn stover at 20% (wt/wt, the corn stover is 20% weight percentage of the total weight of the stover, water, hydrolase and the chemical reagents) substrate concentration. "—■—" represents the sugar concentration of DLA+LHW pretreated corn stover enzymatic hydrolysate; "—●—" represents the sugar concentration of PCS+DA pretreated corn stover enzymatic hydrolysate; "⋯▲⋯" represents the sugar concentration of DA pretreated corn stover enzymatic hydrolysate. Glucose concentration for DLA+LHW reached 73 g/L after 72 h enzymatic hydrolysis, which was higher than 70 g/L for PCS+DA and 68 g/L for DA-CS. The final xylose concentration for DLA+LHW was 32 g/L. In addition, at the point of hydrolysis for 17 hours, the enzymatic hydrolysis results of the three pretreatment methods were close to the maximum concentration, and the hydrolysis rate of DLA+LHW was the fastest within 12 h. The above results show that, compared with PCS+DA and DA, DLA+LHW has the advantages of faster conversion rate and higher yield of hydrolyzed sugars in the process of substrate enzymatic hydrolysis, and has broad application prospects.

Example 8

Example 8 shows the results of enzymatic hydrolysis and fermentation of the DLL+LHW pretreated corn stover at 20% (wt/wt, the corn stover is 20% weight percentage of the total weight of the stover, water, hydrolase and the chemical reagents) enzymatic hydrolysis substrate concentration without detoxification and fed-batch feeding process, which includes the following steps:

1. Raw materials preparation: the corn stover was harvested in the field, dried naturally, and then milled to particles with diameters of 1-4 mm.

2. DLL pretreatment: the milled corn stover was sprayed with calcium hydroxide solution. The dosage of calcium hydroxide was 0.15 g/g dry corn stover biomass. The final water content was 0.5 g/g dry biomass. The corn stover uniformly mixed with the calcium hydroxide was then pelletized in a pellet granulator to perform a densification operation. After the densification, the corn stover was stored in a sealed bag at room temperature for at least one day.

3. DLL+LHW pretreatment: the corn stover densifying pretreated with calcium hydroxide with a calcium hydroxide concentration of 0.15 g/g dry biomass is arranged in a high-temperature and high-pressure reactor for heating, the heating temperature is 140° C., and the reaction time is 60 minute, wherein the dry weight of the stover: the total water is 1:5.

4. Enzymatic hydrolysis process: the pretreated corn stover was enzymatically hydrolyzed at 20% substrate concentration (wt/wt, the corn stover is 20% weight percentage of the total weight of the stover, water, hydrolase and the chemical reagents) with addition of hydrolase and pure water. Enzymatic hydrolysis was performed at 50° C. and 250 rpm in a shake incubator for 72 h.

5. Fermentation process: the obtained enzymatic hydrolysate was fermented using a bacterial strain, which can ferment xylose. The initial optical density (OD) for fermentation was 2.0. Fermentation was carried out in shake flasks at 30° C. and 150 rpm for 72 h.

Figure 10:
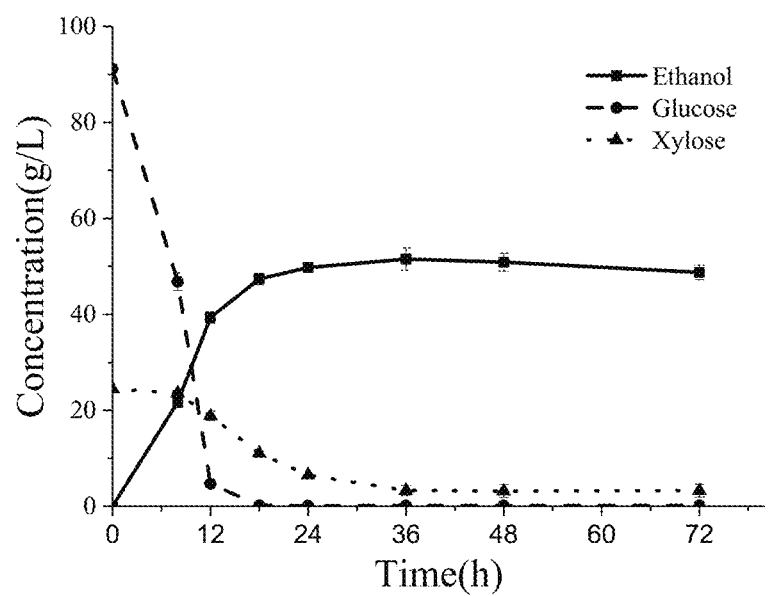
FIG. 10 shows ethanol fermentation curve of the enzymatic hydrolysate of pretreated corn stover without detoxification or batch feeding during hydrolysis at 20% substrate concentration (wt/wt, the corn stover is 20% weight percentage of the total weight of the stover, water, hydrolase and the chemical reagents) in Example 8, before which the corn stover is densifying pretreated with calcium hydroxide added during densification, followed by hot water treatment (DLL+LHW).

Example 8 shows the results of enzymatic hydrolysis and fermentation of the DLL+LHW pretreated corn stover at 20% (wt/wt, the corn stover is 20% weight percentage of the total weight of the stover, water, hydrolase and the chemical reagents) substrate concentration without detoxification and fed-batch feeding process, As shown in FIG. 10, "—●—" represents the glucose concentration of DLL+LHW fermentation broth; "—▲—" represents the xylose concentration of DLL+LHW fermentation broth; "—■—" represents the ethanol concentration of DLL+LHW fermentation broth. After 72 hours of hydrolysis, the enzymatic hydrolysis of DLL+LHW pretreated corn stover resulted in a final glucose concentration of 91.1 g/L and a xylose concentration of 24.4 g/L. In addition, after 36 hours of fermentation, the final ethanol output reached 51.5 g/L, and the final total sugar conversion rate of the fermentation reached over 97%. It can be speculated that the DLL+LHW pretreated corn stover generates inhibitors with a low concentration. In the process without detoxification and fed-batch feeding, the conversion efficiency of sugar and the concentration of ethanol both are high, therefore it has great advantages in the biotransformation process.

Example 9

Example 9 is to show the effect of different enzymatic hydrolysis substrate, DLS pretreated corn stover, on enzymatic hydrolysis, which includes the following steps:

1. Raw materials preparation: the corn stover was harvested in the field, dried naturally, and then milled to particles with diameters of 1-4 mm particles.

2. DLS pretreatment: the milled corn stover was placed in a sealed bag and sprayed uniformly with sodium hydroxide solution. The amount of sodium hydroxide and water used depend on the dry weight of the corn stover. The dosage of the sodium hydroxide was 0.1 g/g dry corn stover biomass, and the water content was 0.1 g/g dry corn stover biomass. The densification process is performed at room temperature, and the DLS pretreated corn stover was stored at room temperature for at least one day.

3. DLS+Autoclave pretreatment: the corn stover densifying pretreated with sodium hydroxide with a sodium hydroxide dosage of 0.1 g/g dry corn stover biomass was autoclaved at 120° C. for 60 min in a shake flask with pure water addition to reach the dry corn stover biomass solid loading of 30% (wt/wt, based on the total weight).

4. Enzymatic hydrolysis process: DLS+Autoclave pretreated corn stover was enzymatically hydrolyzed in an enzymatic hydrolysis reactor at 3%, 6%, and 9% (wt/wt, the weight percentage of glucan in the total weight of the stover, water, hydrolase and the chemical reagents) glucan concentration with addition of hydrolase and Citrate buffer. Enzymatic hydrolysis was performed at 50° C. and 250 rpm in a shake incubator for 72 h.

Figure 9:
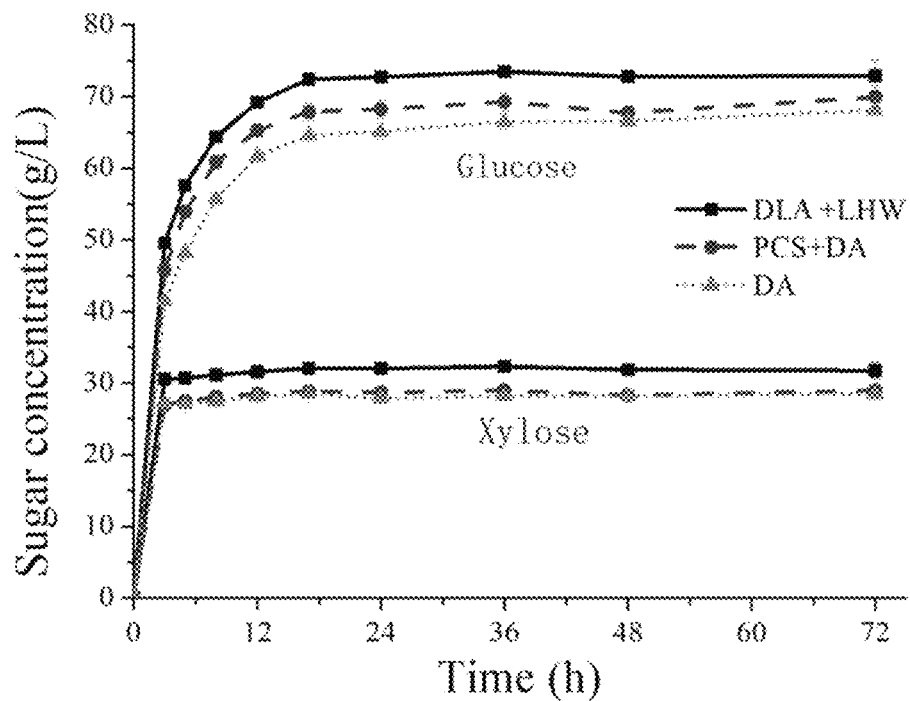
FIG. 9 shows the sugar concentration with hydrolysis time during enzymatic hydrolysis of the corn stover at 20% substrate concentration (wt/wt, corn stover is 20% weight percentage of the total weight of the stover, water, hydrolase and the chemical reagents) in Example 7, before which the corn stover is densifying pretreated with an acid added during densification, followed by further treated with hot water (DLA+LHW), or densified and then pretreated with dilute acid (PCS+DA), or pretreated with dilute acid (DA).
Figure 11:
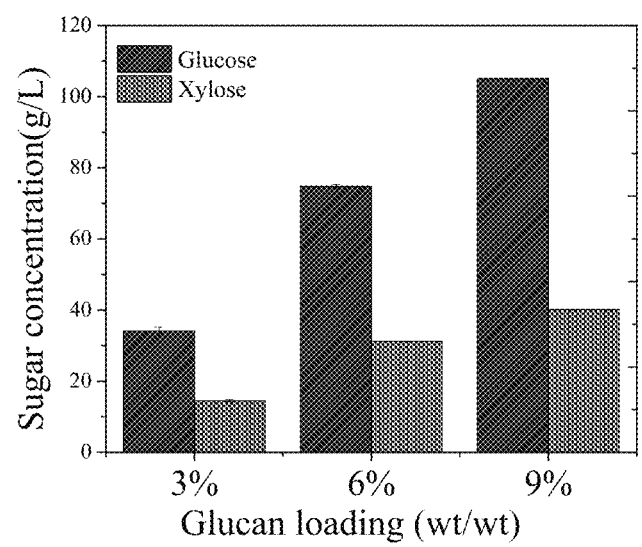
FIG. 11 shows the sugar concentrations for 72 hours enzymatic hydrolysis at different substrate solid loadings of the corn stover densified with sodium hydroxide followed with sterilization (DLS+Auctoclave).

Example 9 shows the effect of different enzymatic hydrolysis substrate, DLS pretreated corn stover, on enzymatic hydrolysis. As shown in FIG. 11, "▨" represents the glucose concentration from enzymatically hydrolysis of DLS+Auctoclave pretreated corn stover; "▨" represents the xylose concentration from enzyme hydrolysis of DLS+Auctoclave pretreated corn stover. It can be seen from FIG. 9 that after the corn stover is densified with sodium hydroxide, as the concentration of the enzymatic hydrolysis substrate increases, the concentrations of glucose and xylose in the enzyamtic hydrolysis increases, and under the condition of 9% glucan substrate, the glucose concentration in enzymatic hydrolysate reached 105.1 g/L, and the concentration of xylose was 40.1 g/L. The total sugar concentration reached 145.2 g/L, which represents the potential of bioconversion into high ethanol concentration.

The invention claimed is:

1. A method for pretreating a lignocellulose with an alkaline reagent(s) or an acidic reagent(s) during densification, comprising:
    adding the alkaline reagent(s) or acidic reagent(s) during the densification of a lignocellulose raw material to obtain an acid- or base-containing densified lignocellulose with a density of 200-1500 kg/m$^3$ and a moisture content of 31.3% or less.

2. A method for bio-transforming an acid- or base-containing densified lignocellulose, comprising:
    adding the alkaline reagent(s) or acidic reagent(s) during the densification of a lignocellulose raw material
    to obtain an acid- or base-containing densified lignocellulose with a density of 200-1500 kg/m$^3$ and a moisture content of 31.3% or less, which can be directly bio-transformed or further selectively pretreated for a subsequent bio-transformation.

3. The method of claim 1, characterized in that:
    the lignocellulose is selected from one or more of the following: wheat straw, corn stover, rice straw, sorghum stover, soybean stover, recycled wood pulp fiber, wood chips, softwood, hardwood, aquatic weed, algae, animal feces and combinations thereof.

4. The method of claim 1, characterized in that:
    the alkaline reagent(s) is selected from one or more of the following: sodium hydroxide, calcium hydroxide, potassium hydroxide, sodium sulphite, sodium bisulfite, sodium acetate, sodium carbonate, sodium bicarbonate, sodium sulfate, ethylenediamine, triethylamine, ammonia water, liquid ammonia, calcium oxide, sodium oxide, and combinations thereof.

5. The method of claim 1, characterized in that:
the acidic reagent(s) is selected from one or more of the following: sulfuric acid, nitric acid, nitrous acid, hydrochloric acid, phosphoric acid, sulphurous acid, perchloric acid, chloric acid, chlorous acid, hypochlorous acid, oxalic acid, formic acid, acetic acid, propionic acid, benzoic acid, phenylacetic acid, benzenesulfonic acid, oxalic acid, succinic acid, carbon dioxide, sulfur dioxide, sodium bisulfate, sodium bisulfite, and combinations thereof.

6. The method of claim 1, characterized in that:
the dosage of the alkaline reagent(s) or acidic reagent(s) is in the range of 0.5%~30.0% by weight of the lignocellulose.

7. The method of claim 1, characterized in that:
the alkaline reagent(s) or acidic reagent(s) can be directly added in the form of pure base reagent(s) or acidic reagent(s), or in the form of an aqueous solution of the base or acidic reagent(s).

8. The method of claim 1, characterized in that:
the alkaline reagent(s) or acidic reagent(s) can be directly poured or added, sprayed, brought in via steam, or sprayed as an alkaline or acidic gas, such that the alkaline or acidic reagent(s) can be fully mixed with the lignocellulose for performing a lignocellulose densification treatment; or during the densification, the alkaline reagent(s) or acidic reagent(s) and the lignocellulose are added to a densification equipment to produce a densified lignocellulose with a dense shape.

9. The method of claim 2, characterized in that:
the acid- or base-containing densified lignocellulose without further pretreatment can be subjected to biotransformation immediately or after standing for a certain period of time.

10. The method of claim 2, characterized in that:
the acid- or base-containing densified lignocellulose can be further selectively pretreated for the subsequent biotransformation, and the further selective pretreatment of densified lignocellulose is selected from the following: spraying water on the lignocellulose, steaming, soaking, sun exposure, freezing, high temperature treatment, cooking in water, high temperature sterilization, microwave, ultrasonic treatment, steam explosion, hot water pretreatment, steam pretreatment, dilute acid pretreatment, weak acid pretreatment, oxidative acid pretreatment, mixed acid pretreatment, dilute alkaline pretreatment, weak alkaline pretreatment, ammonia pretreatment, oxidative alkaline pretreatment, mixed alkaline pretreatment, or organic solvent pretreatment.

11. The method of claim 1, characterized in that:
the densified lignocellulose has a rod shape with a diameter of 1 mm-30 cm; a granule shape with a diameter of 0.1 cm-50 cm;
a block shape with a length of 0.1 cm-200 cm, a width of 0.1 cm-200 cm, and a height of 0.1 cm-200 cm; or a pellet shape with a diameter of 0.1 cm-50 cm and a thickness of 0.01 cm-20 cm.

12. The method of claim 2, characterized in that:
the biological transformation comprises:
an enzymatic reaction comprising adding enzymes or fermentation in a pretreatment substrate, wherein the enzyme is selected from one or more of cellulase, hemicellulase, pectinase, xylanase, amylase and saccharification enzyme, and/or
a microbial transformation which is a microorganism fermentation comprising adding a fermenting microorganism into a pretreatment substrate or enzymatic hydrolysate, and the fermenting microorganism is selected from one or more of yeast, bacteria, and mold.

13. The method of claim 2, characterized in that:
the biotransformation has a product comprising biofuels, commodity chemicals, fine chemicals, animal feeds, food additives or medicines.

14. The method of claim 13, characterized in that:
the product is selected from ethanol, butanol, acetone, acetic acid, lactic acid, aliphatic hydrocarbon, lipids, proteins, amino acids, enzymes, antibiotics, vitamins, antibodies, and methane.

15. The method of claim 2, characterized in that:
the lignocellulose is selected from one or more of the following: wheat straw, corn stover, rice straw, sorghum stover, soybean stover, recycled wood pulp fiber, wood chips, softwood, hardwood, aquatic weed, algae, animal feces and combinations thereof.

16. The method of claim 2, characterized in that:
the alkaline reagent(s) is selected from one or more of the following: sodium hydroxide, calcium hydroxide, potassium hydroxide, sodium sulphite, sodium bisulfate, sodium acetate, sodium carbonate, sodium bicarbonate, sodium sulfate, ethylenediamine, triethylamine, ammonia water, liquid ammonia, calcium oxide, sodium oxide, and combinations thereof.

17. The method of claim 2, characterized in that:
the acidic reagent(s) is selected from one or more of the following: sulfuric acid, nitric acid, nitrous acid, hydrochloric acid, phosphoric acid, sulphurous acid, perchloric acid, chloric acid, chlorous acid, hypochlorous acid, oxalic acid, formic acid, acetic acid, propionic acid, benzoic acid, phenylacetic acid, benzenesulfonic acid, oxalic acid, succinic acid, carbon dioxide, sulfur dioxide, sodium bisulfate, sodium bisulfate, and combinations thereof.

18. The method of claim 2, characterized in that:
the dosage of the alkaline reagent(s) or acidic reagent(s) is in the range of 0.5%~30.0% by weight of the lignocellulose.

19. The method of claim 2, characterized in that:
the alkaline reagent(s) or acidic reagent(s) can be directly added in the form of pure base reagent(s) or acidic reagent(s), or in the form of an aqueous solution of the base or acidic reagent(s).

20. The method of claim 2, characterized in that:
the alkaline reagent(s) or acidic reagent(s) can be directly poured or added, sprayed, brought in via steam, or sprayed as an alkaline or acidic gas, such that the alkaline or acidic reagent(s) can be fully mixed with the lignocellulose for performing a lignocellulose densification treatment; or during the densification, the alkaline reagent(s) or acidic reagents) and the lignocellulose are added to a densification equipment to produce a densified lignocellulose with a dense shape.

* * * * *